(12) United States Patent
Zhao et al.

(10) Patent No.: US 10,803,354 B2
(45) Date of Patent: Oct. 13, 2020

(54) CROSS-MODALITY IMAGE SYNTHESIS

(71) Applicant: Siemens Healthcare GmbH, Erlangen (DE)

(72) Inventors: Yu Zhao, Athens, GA (US); Yimo Gao, Chester Springs, PA (US); Shu Liao, Chester Springs, PA (US); Liang Zhao, Shanghai (CN); Zhennan Yan, West Windsor, NJ (US); Yiqiang Zhan, West Chester, PA (US); Xiang Sean Zhou, Exton, PA (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/258,751

(22) Filed: Jan. 28, 2019

(65) Prior Publication Data

US 2019/0311228 A1    Oct. 10, 2019

(30) Foreign Application Priority Data

Apr. 5, 2018   (EP) .................................... 18165851

(51) Int. Cl.
   *G06K 9/62*      (2006.01)
   *G06K 9/32*      (2006.01)
   (Continued)

(52) U.S. Cl.
   CPC .............. *G06K 9/6256* (2013.01); *A61B 6/03* (2013.01); *G06K 9/3233* (2013.01);
   (Continued)

(58) Field of Classification Search
   CPC ...... G06K 9/3233; G06K 9/6256; A61B 6/03; A61B 6/5235; A61B 6/5247;
   (Continued)

(56) References Cited

U.S. PATENT DOCUMENTS

| 9,878,178 B2 | 1/2018 | Schweizer |
| 2008/0170770 A1* | 7/2008 | Suri .......................... A61B 8/12 382/128 |

(Continued)

FOREIGN PATENT DOCUMENTS

| DE | 102015213730 A1 | 1/2017 |
| WO | 2015103184 A1 | 7/2015 |
| WO | 2018048507 A1 | 3/2018 |

*Primary Examiner* — Ali Bayat (57) ABSTRACT

A framework for cross-modality image synthesis. A first and second model may be trained using respective first and second pairs of complementary images and corresponding first and second ground truth images that represent first and second views of a region of interest. The first and second pairs of complementary images may be acquired by a first modality and the first and second ground truth images may be acquired by a second modality. A combinational network may further be trained to combine features from the first and second models. At least one synthetic second modality image may then be generated by passing current images through the trained first or second model and the combinational network, wherein the current images are acquired by the first modality and represent the first or second view of the region of interest.

20 Claims, 6 Drawing Sheets

(51) Int. Cl.
*G06N 3/04* (2006.01)
*G06T 7/00* (2017.01)
*A61B 6/03* (2006.01)
*G06T 11/00* (2006.01)

(52) U.S. Cl.
CPC ......... *G06N 3/0454* (2013.01); *G06T 7/0014* (2013.01); *G06T 11/008* (2013.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01)

(58) Field of Classification Search
CPC ..... A61B 5/0035; A61B 5/055; A61B 5/7267; G06N 3/0454; G06T 7/0014; G06T 11/008; G06T 2207/10081; G06T 2207/10088; G06T 2207/10104; G06T 2207/10108; G06T 2207/20081; G06T 2207/20084
USPC ........................................................ 382/159
See application file for complete search history.

(56) References Cited

U.S. PATENT DOCUMENTS

| | | | |
|---|---|---|---|
| 2010/0198063 A1* | 8/2010 | Huber | A61B 8/12 600/437 |
| 2016/0210749 A1 | 7/2016 | Nguyen et al. | |
| 2016/0314600 A1 | 10/2016 | Nguyen et al. | |
| 2018/0249979 A1* | 9/2018 | Wang | G01R 33/3815 |
| 2018/0374194 A1* | 12/2018 | Park | G06T 3/0081 |
| 2019/0244399 A1* | 8/2019 | Li | G01R 33/5611 |
| 2019/0370965 A1* | 12/2019 | Lay | G06N 20/00 |
| 2020/0034948 A1* | 1/2020 | Park | A61N 5/1067 |

\* cited by examiner

CROSS-MODALITY IMAGE SYNTHESIS

CROSS REFERENCE TO RELATED APPLICATIONS

This application claims priority to EP Patent Application No. 18165851.9 filed on Apr. 5, 2018, the contents of which are incorporated by reference.

TECHNICAL FIELD

The present disclosure generally relates to digital image data processing, and more particularly to cross-modality image synthesis.

BACKGROUND

The field of medical imaging has seen significant advances since the time X-Rays were first used to determine anatomical abnormalities. Medical imaging hardware has progressed from modern machines, such as Magnetic Resonance (MR) imaging scanners, Computed Tomographic (CT) scanners and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Digital medical images are constructed using raw image data obtained from a scanner, for example, a computerized axial tomography (CAT) scanner, magnetic resonance imaging (MRI), etc. Digital medical images are typically either a two-dimensional ("2D") image made of pixel elements, a three-dimensional ("3D") image made of volume elements ("voxels") or a four-dimensional ("4D") image made of dynamic elements ("doxels"). Such 2D, 3D or 4D images are processed using medical image recognition techniques to determine the presence of anatomical abnormalities or pathologies, such as cysts, tumors, polyps, etc. Given the amount of image data generated by any given image scan, it is preferable that an automatic technique should point out anatomical features in the selected regions of an image to a doctor for further diagnosis of any disease or condition.

Automatic image processing and recognition of structures within a medical image are generally referred to as Computer-Aided Detection (CAD). A CAD system can process medical images, localize and segment anatomical structures, including possible abnormalities (or candidates), for further review. Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor in order to reach an early diagnosis.

MR images play an important role in successful radiotherapy, providing both excellent soft-tissue contrast for target delineation and density information for treatment planning. MR imaging does not involve X-rays and the use of ionizing radiation, which distinguishes it from CT scans. MR images often yield different diagnostic information compared to CT image. CT images may be necessary in some cases for providing electron density information for dose calculation in treatment planning. The acquisition and use of CT images for treatment planning, however, is typically associated with extra costs and time.

SUMMARY

Described herein is a framework for cross-modality image synthesis. In accordance with one aspect, a first model is trained using first pairs of complementary images and corresponding first ground truth images. The first pairs of complementary images may be acquired by a first modality and the first ground truth images may be acquired by a second modality. The first pairs of complementary images and the first ground truth images may represent a first view of a region of interest. A second model may further be trained using second pairs of complementary images and corresponding second ground truth images. The second pairs of complementary images may be acquired by the first modality and the second ground truth images may be acquired by the second modality. The second pairs of complementary images and the second ground truth images represent a second view of the region of interest. A combinational network may be trained to combine features from the first and second models. At least one synthetic second modality image may then be generated by passing current images through the trained first or second model and the combinational network, wherein the current images are acquired by the first modality and represent the first or second view of the region of interest.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to high-resolution computed tomography (HRCT), x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

In a traditional MR-CT imaging workflow, CT images are first acquired, followed by MR images. Registration, delineation and radiotherapy dose planning may then be performed based on the MR and/or CT images. The workflow for acquiring and using only MR images is much shorter and more efficient than the MR/CT imaging workflow. CT images may be synthesized from MR images to fulfill the MR-only workflow. The MR-only imaging workflow typically involves acquiring MR images, synthesizing CT images based on the MR images, delineation and radiotherapy dose planning. It is, however, very challenging to precisely synthesize soft tissues and bone areas directly from MR images. Popular techniques include using an atlas-based approach or deformable models to borrow CT image information from a patient population to generate synthetic CT image for the underlying patient. This challenge has not been satisfactorily resolved yet, and the existing synthesis workflows are too time-consuming (~10 min for a single volume).

A framework for automatic cross-modality image synthesis is described herein. One aspect of the framework is based on deep learning multiple-channel multiple-view networks. Two different sequences of images acquired by one modality (e.g., MR) may be provided as training inputs to the networks. The two image sequences may represent two different views (e.g., sagittal and axial views) of a 3D image volume. The two image sequences provide complementary information for precise synthesis of the output image. The networks may be combined to synthesize images for another different modality (e.g., CT).

Instead of using a dual-modality (e.g., MR and CT) workflow for radiotherapy planning, the present cross-modality image synthesis framework advantageously enables a single-modality (e.g., MR-only) workflow to parse, for example, both soft tissue and bone areas. The present framework has achieved much higher precision and runtime efficiency (e.g., within 10 seconds) for a single volume synthesis.

It should be appreciated that the present framework is not limited to the image modalities and/or anatomies described herein but is applicable to other kinds of cross-modality image synthesis applications. These and other features and advantages will be described in more details herein.

Figure 1:
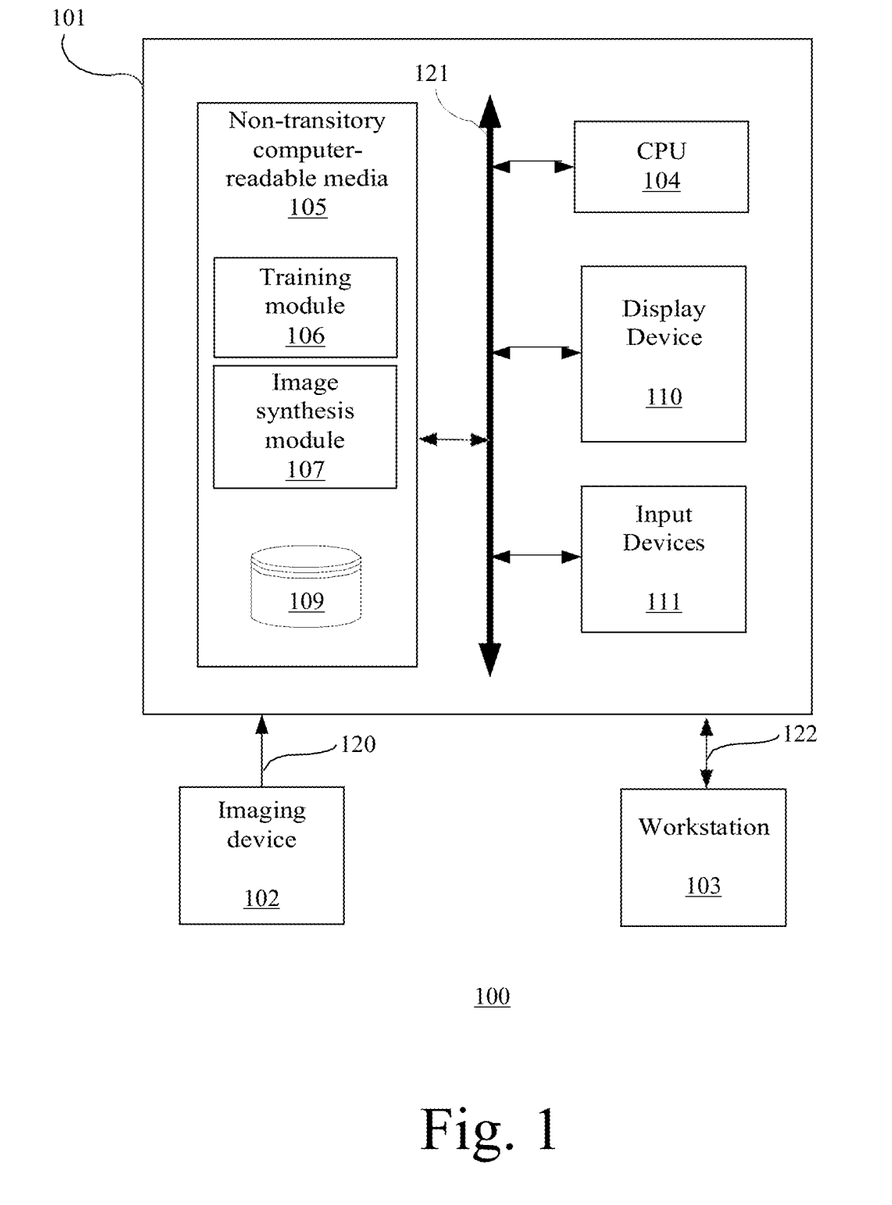
FIG. 1 is a block diagram illustrating an exemplary system.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server), a cloud computing platform, a client user machine in server-client user network environment, or as a peer machine in a peer-to-peer (or distributed) network environment.

In some implementations, computer system 101 comprises a processor or central processing unit (CPU) 104 coupled to one or more non-transitory computer-readable media 105 (e.g., computer storage or memory), display device 110 (e.g., monitor) and various input devices 111 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 105. In particular, the present techniques may be implemented by training module 106, image synthesis module 107 and database 109.

Non-transitory computer-readable media 105 may include random access memory (RAM), read-only memory (ROM), magnetic floppy disk, flash memory, and other types of memories, or a combination thereof. The computer-readable program code is executed by CPU 104 to process medical data retrieved from, for example, database 109. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 109. Such data may also be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 102 acquires medical images 120 associated with at least one patient. Such medical images 120 may be processed and stored in database 109. Imaging device 102 may be a radiology scanner (e.g., MR scanner) and/or appropriate peripherals (e.g., keyboard and display device) for acquiring, collecting and/or storing such medical images 120.

The workstation 103 may include a computer and appropriate peripherals, such as a keyboard and display device, and can be operated in conjunction with the entire system 100. For example, the workstation 103 may communicate directly or indirectly with the imaging device 102 so that the medical image data acquired by the imaging device 102 can be rendered at the workstation 103 and viewed on a display device. The workstation 103 may also provide other types of medical data 122 of a given patient. The workstation 103 may include a graphical user interface to receive user input via an input device (e.g., keyboard, mouse, touch screen voice or video recognition interface, etc.) to input medical data 122.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
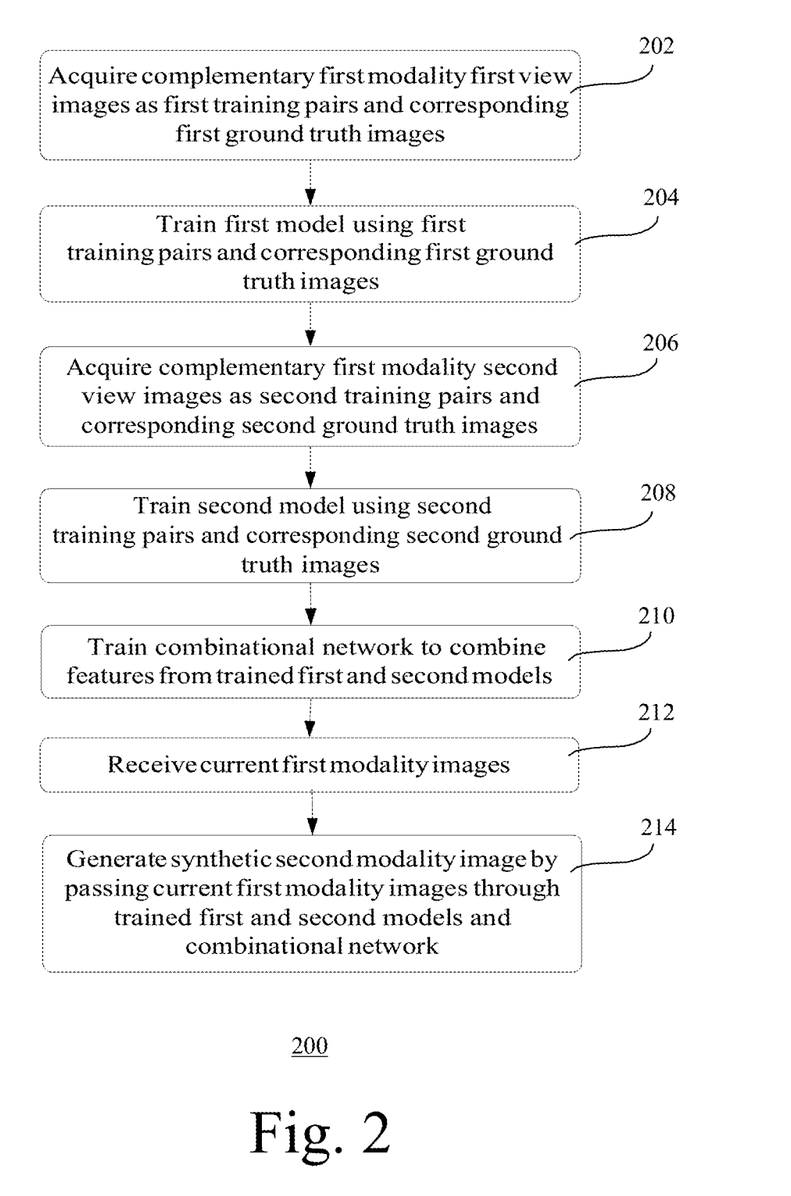
FIG. 2 shows an exemplary method of cross modality image synthesis by a computer system.

FIG. 2 shows an exemplary method 200 of image synthesis by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 202, training module 106 acquires complementary first modality first view images as first training pairs and corresponding first ground truth images. The first training pairs and corresponding first ground truth images may be retrieved from, for example, database 109 and/or acquired by imaging device 102. The complementary first modality first view 2D images may be extracted from 3D image data of a region of interest acquired using a first modality.

The complementary first modality first view images may be image sequences that provide multi-channel complementary information for image synthesis. For example, the complementary first modality first view images may include an in-phase MR image sequence and a corresponding out-of-phase MR image sequence. Other types of complementary image sequences are also useful. The complementary first modality first view images represent a first view of a region of interest. The first view may be a sagittal view or another type of view, such as coronal or axial view. The region of interest may be a body portion that has been identified for investigation. The region of interest may be, for example, at least a section of a subject's elbow, spine, vertebra, brain, chest, and so forth.

The first ground truth images correspond to the complementary first modality first view images. The first ground truth images may be extracted by 3D image data of the region of interest acquired by a second modality. The first ground truth images represent the first view of the region of interest and may be, for example, two-dimensional (2D). The first ground truth images may be used as ground truth to check the accuracy of the first model's output during the training phase.

In some implementations, the first and second modalities are different. For example, the first and second modalities may be MR and CT respectively. Other types of combinations of first and second modalities are also useful. For example, the first and second modalities may be CT and MR respectively. Alternatively, the first and second modalities are the same or similar. For example, the first and second modalities may both be MR or CT. It should also be appreciated that other types of modalities, such as high-resolution computed tomography (HRCT), helical CT, X-ray, angiography, positron emission tomography (PET), fluoroscopy, ultrasound, single photon emission computed tomography (SPECT), or a combination thereof, may be used.

At 204, training module 106 trains a first model using the first training pairs and corresponding first ground truth images. In some implementations, the first model is an unsupervised learning structure that automatically discovers representations needed for feature detection instead of relying on labeled input. The first model may be a deep learning architecture that includes stacked layers of learning nodes. The first model may be represented by, for example, a convolutional neural network (CNN) classifier.

CNN is a class of deep, feed-forward artificial neural network that uses a variation of multilayer perceptrons designed to require minimal preprocessing. Other types of classifiers, such as random forests, may also be used. The CNN model may include an input layer, an output layer, as well as multiple hidden layers. The hidden layers are either convolutional, pooling or fully connected. Convolutional layers apply a convolution operation to the input, passing the result to the next layer, thereby emulating the response of an individual neuron to visual stimuli. Pooling layers combine the outputs of neuron clusters at one layer into a single neuron in the next layer, while fully connected layers connect every neuron in one layer to every neuron in another layer. The pooling layers may employ max pooling, which uses the maximum value from each of a cluster of neurons at the prior layer. Different loss functions, such as Mean Squared Error (MSE), Huber L1 or hinge-like loss functions, may be combined with the maxpooling process to improve the network output quality.

Figure 3:
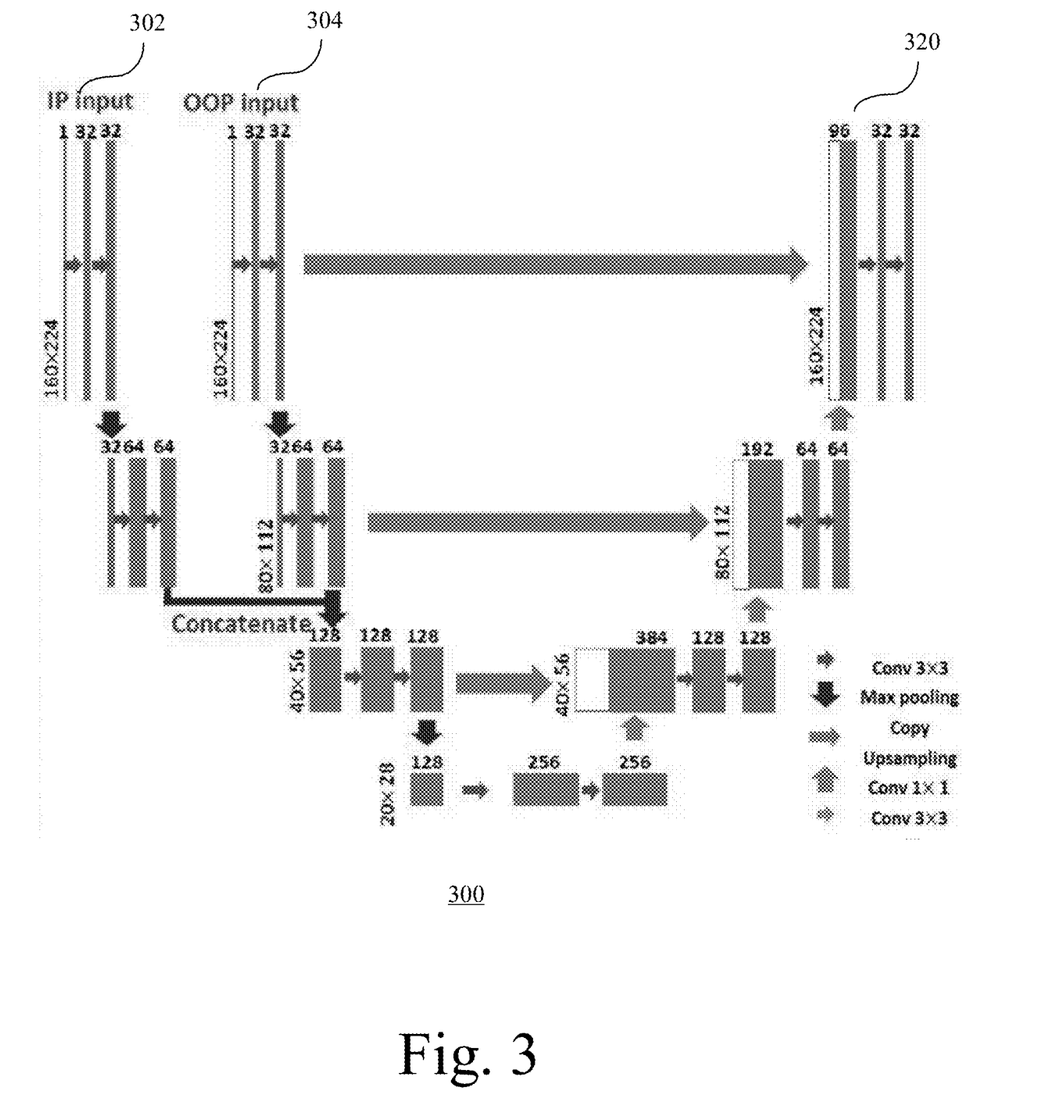
FIG. 3 shows an exemplary first model.

FIG. 3 shows an exemplary first model 300. The first training pair (302, 304) includes a pair of MR in-phase (IP) and out-of-phase (OOP) images that are passed into the first model 300 as input. The goal of this first model 300 is to synthesize a CT image 320 from IP and OOP images (302, 304) that represent the first view (e.g., axial view). A feature map may be generated based on the output CT image 320. The IP and OOP images (302, 304) go through a series of convolutional operations, followed by downsampling procedures to extract anatomical information at different resolutions. The IP and OOP images are then upsampled and go through a series of convolution operations again to restore the original resolution and create the final output CT image 320. The total training process may take, for example, 250 epochs.

Returning to FIG. 2, at 206, training module 106 acquires complementary first modality second view images as second training pairs and corresponding second ground truth images. The second training pairs and corresponding second ground truth images may be retrieved from, for example, database 109 and/or acquired by imaging device 102. The complementary first modality second view images may be 2D images extracted from 3D image data of a region of interest acquired using the first modality.

The complementary first modality second view images may be image sequences that provide multi-channel complementary information for image synthesis. For example, the complementary first modality second view images may include an in-phase MR image sequence and a corresponding out-of-phase MR image sequence. Other types of complementary image sequences are also useful. The complementary first modality second view images represent a second view of a region of interest. The second view may be different from the first view. For example, the second view may be an axial view while the first view may be a sagittal view of the region of interest. Other combinations or types of views, such as coronal or sagittal views, may also be useful.

The second ground truth images correspond to the complementary first modality second view images. The second ground truth images may be extracted by 3D image data of the region of interest acquired by a second modality. The second ground truth images represent the second view of the region of interest and may be, for example, two-dimensional (2D). The second ground truth images may be used as ground truth to check the accuracy of the second model's output during the training phase.

At 208, training module 106 trains a second model using the second training pairs and corresponding second ground truth images. In some implementations, the second model is an unsupervised learning structure that automatically discovers representations needed for feature detection instead of relying on labeled input. The second model may be a deep learning architecture that includes stacked layers of learning nodes. The second model may be similar to the first model, and may be represented by, for example, a convolutional neural network (CNN) classifier.

Figure 4:
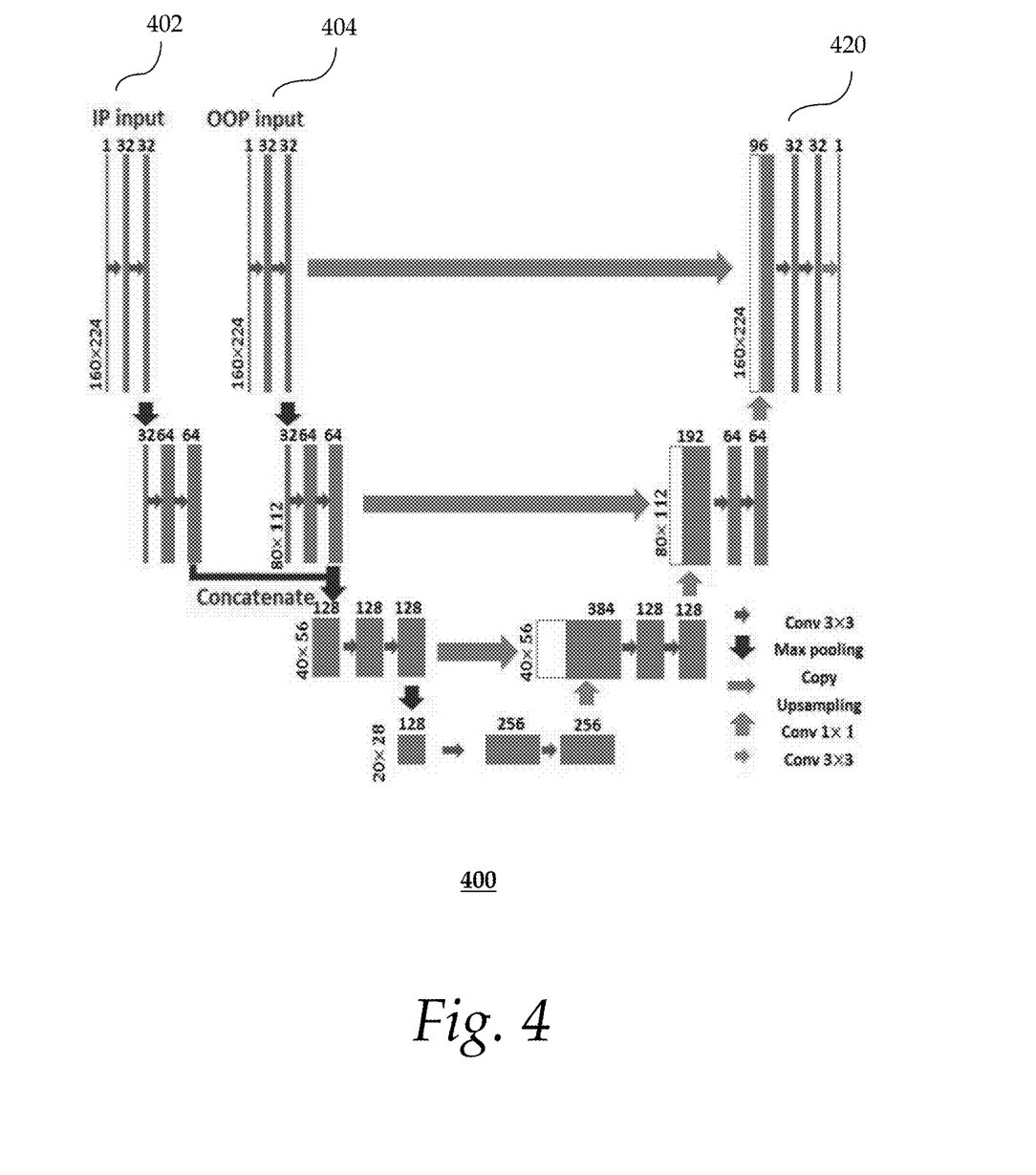
FIG. 4 shows an exemplary second model.

FIG. 4 shows an exemplary second model 400. The second training pair (402, 404) includes a pair of MR in-phase (IP) and out-of-phase (OOP) images that are passed into the second model 400 as input. The goal of this second model 400 is to synthesize a CT image 420 from IP and OOP images (402, 404) that represent the second view (e.g., sagittal view). A feature map may be generated based on the output CT image 420. The second model 400 is similar to first model 300 as described with reference to FIG. 3. The total training process may take, for example, 250 epochs.

Returning to FIG. 2, at 210, training module 106 trains a combinational network to combine (or concatenate) feature maps generated by the first and second models and generate a synthetic second modality output image. The combinational network may combine the feature maps generated by the first and second models to remove the blurring effects caused by stitching 2D slides in 3D views. The combinational network may include, but not limited to, a simple one-layer network, fully convolutional network, U net or a residual network.

Figure 5:
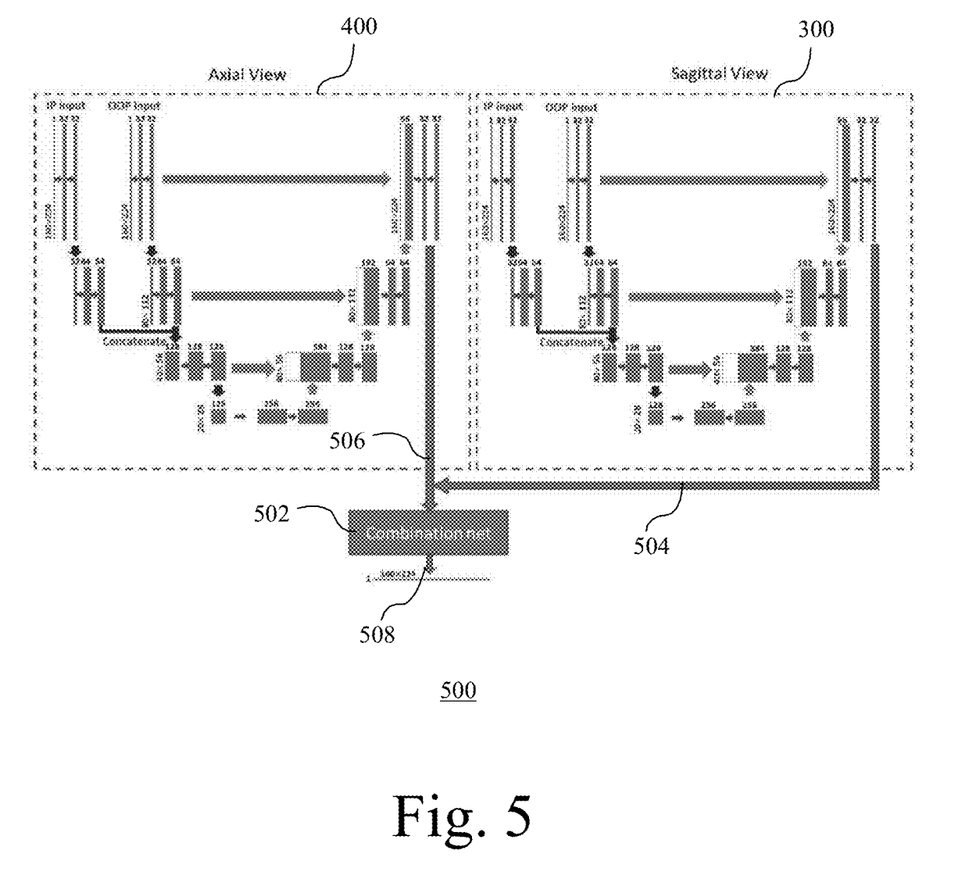
FIG. 5 shows an overview of an exemplary multi-channel multi-view network structure.

FIG. 5 shows an overview of an exemplary multi-channel multi-view network structure 500. The network structure 500 includes a first model 300 trained based on 2D slices in sagittal view, a second model 400 trained based on 2D slices in axial view and a combinational network 502. The combinational network 502 is trained to combine multi-view features (504, 506) extracted from the first and second models (300, 400) to synthesize an output image 508 in the second modality wherein the 2D stitching effects introduced by the 2D models (300, 400) are removed. The output image 508 may be, for example, 2D. A series of 2D output images may be stacked to generate a final 3D synthetic image volume. The total training process may take, for example, 100 epochs. It should be appreciated that the trained first and second models, as well as the combinational network, may be further fine-tuned to improve the output quality when more training pairs are available.

Returning to FIG. 2, at 212, image synthesis module 107 receives current first modality images. The current first modality images may be received during testing or runtime. The current first modality images may be acquired by the same imaging modality (i.e., first modality) as the first and second training pairs used for training the first and second models. Additionally, the current first modality images may include complementary image data (e.g., in-phase and outof-phase MR image data) for providing complementary information. The current first modality images may be 2D images extracted from current 3D image data acquired by the first modality.

The current first modality images may include one or more images that represent a first view, which is the same view (e.g., sagittal) represented by the first training pairs and corresponding first ground truth images used to train the first model. Additionally, or alternatively, the current first modality images may also include one or more images that represent the second view, which is the same view (e.g., axial) represented by the second training pairs and corresponding second ground truth images used to train the second model.

At 214, image synthesis module 107 generates at least one synthetic second modality image by passing the current first modality images through the trained first and second models and combinational network. Image synthesis module 107 loads weights trained from the first and second models, as well as the combinational network, for generating the synthetic second modality images. In some implementations, current complementary (e.g., in-phase and out-of-phase MR) first view (e.g., axial view) 2D images are input and passed through the trained first model, while current complementary second view (e.g., sagittal view) 2D images are input and passed through the trained second model. The trained combinational network then generates the synthetic second modality images as output. The synthetic second modality image imitates or simulates the features of the first and second ground truth images acquired by the second modality (e.g., CT). The synthetic second modality image may also represent the same view as the input 2D images.

Figure 6:
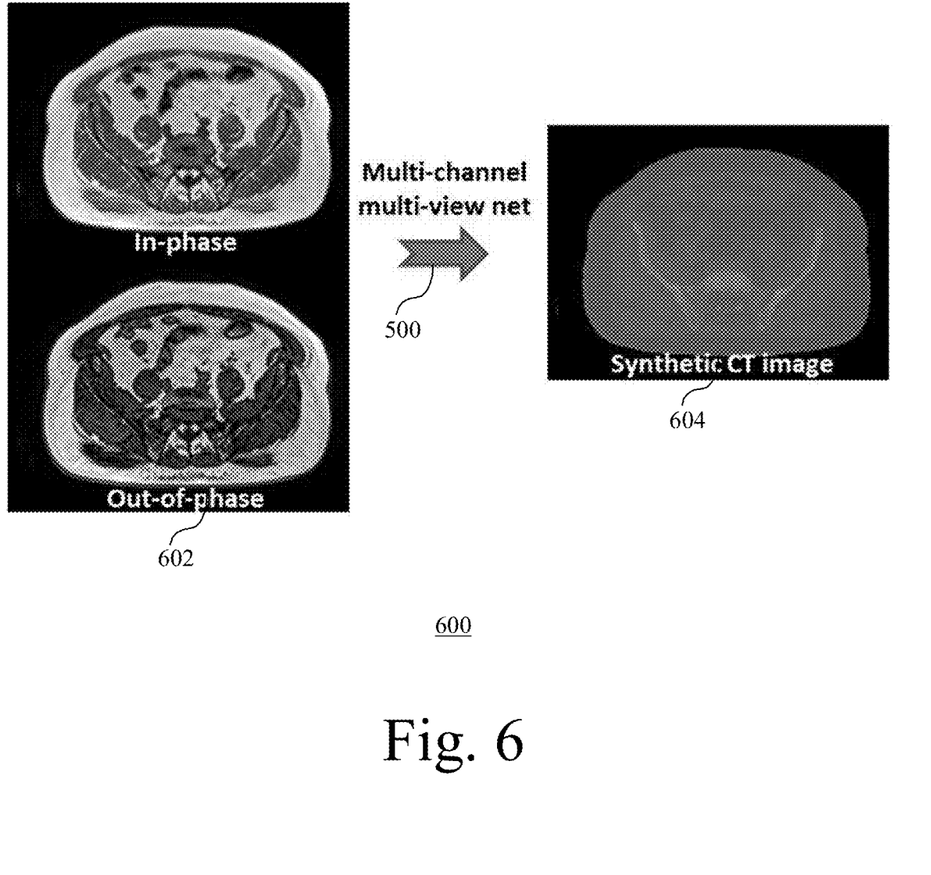
FIG. 6 illustrates an exemplary MR to CT image synthesis process.

FIG. 6 illustrates an exemplary MR to CT image synthesis process 600. A pair of current in-phase and out-of-phase axial view MR images 602 are fed as input to a trained multiple-channel multiple-view network 500. The trained multiple-channel multiple-view network 500 then automatically generates the soft tissue and bone areas of a synthetic axial view CT image 604. The synthetic axial view CT image 604 may be generated in a very short time (e.g., approximately 10 seconds).

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for image synthesis, comprising:
a non-transitory memory device for storing computer readable program code; and
a processor device in communication with the memory device, the processor being operative with the computer readable program code to perform steps including
training a first model using first pairs of complementary images and corresponding first ground truth images, wherein the first pairs of complementary images are acquired by magnetic resonance (MR) imaging and the first ground truth images are acquired by computed tomography (CT), wherein the first pairs of complementary images and the first ground truth images represent a first view of a region of interest,
training a second model using second pairs of complementary images and corresponding second ground truth images, wherein the second pairs of complementary images are acquired by MR imaging and the second ground truth images are acquired by CT, wherein the second pairs of complementary images and the second ground truth images represent a second view of the region of interest
training a combinational network to combine features from the first and second models, and
generating at least one synthetic CT image by passing current MR images through the trained first or second model and the combinational network, wherein the current MR images represent the first or second view of the region of interest.

2. The system of claim 1 wherein the first view comprises an axial view.

3. The system of claim 2 wherein the second view comprises a sagittal view.

4. The system of claim 1 wherein the first and second pairs of complementary images comprise in-phase and out-of-phase MR images.

5. A method for image synthesis, comprising:
training a first model using first pairs of complementary images and corresponding first ground truth images, wherein the first pairs of complementary images are acquired by a first modality and the first ground truth images are acquired by a second modality, wherein the first pairs of complementary images and the first ground truth images represent a first view of a region of interest;
training a second model using second pairs of complementary images and corresponding second ground truth images, wherein the second pairs of complementary images are acquired by the first modality and the second ground truth images are acquired by the second modality, wherein the second pairs of complementary images and the second ground truth images represent a second view of the region of interest;
training a combinational network to combine features from the first and second models; and
generating at least one synthetic second modality image by passing current images through the trained first or second model and the combinational network, wherein the current images are acquired by the first modality and represent the first or second view of the region of interest.

6. The method of claim 5 further comprises acquiring the first and second pairs of complementary images by magnetic resonance (MR) imaging.

7. The method of claim 6 further comprises acquiring the corresponding first and second ground truth images by computed tomography (CT).

8. The method of claim 6 further comprises acquiring the corresponding first and second ground truth images by magnetic resonance (MR) imaging.

9. The method of claim 5 further comprises acquiring the first and second pairs of complementary images by magnetic resonance (MR) in-phase and out-of-phase imaging.

10. The method of claim 5 further comprises acquiring the first and second pairs of complementary images by high-resolution computed tomography (HRCT), helical CT, X-ray, angiography, positron emission tomography (PET), fluoroscopy, ultrasound, single photon emission computed tomography (SPECT), or a combination thereof.

11. The method of claim 5 further comprises acquiring the corresponding first and second ground truth images by high-resolution computed tomography (HRCT), helical CT, X-ray, angiography, positron emission tomography (PET), fluoroscopy, ultrasound, single photon emission computed tomography (SPECT), or a combination thereof.

12. The method of claim 5 wherein the first pairs of complementary images and the first ground truth images represent an axial view of the region of interest.

13. The method of claim 5 wherein the second pairs of complementary images and the second ground truth images represent a sagittal view of the region of interest.

14. The method of claim 5 wherein the first model comprises a first convolutional neural network classifier.

15. The method of claim 5 wherein the second model comprises a second convolutional neural network classifier.

16. The method of claim 5 wherein the combinational network comprises a simple one-layer network.

17. The method of claim 5 further comprises stacking multiple synthetic second modality images to generate a three-dimensional synthetic image volume.

18. One or more non-transitory computer-readable media embodying instructions executable by machine to perform operations, comprising:
  training a first model using first pairs of complementary images and corresponding first ground truth images, wherein the first pairs of complementary images are acquired by a first modality and the first ground truth images are acquired by a second modality, wherein the first pairs of complementary images and the first ground truth images represent a first view of a region of interest;
  training a second model using second pairs of complementary images and corresponding second ground truth images, wherein the second pairs of complementary images are acquired by the first modality and the second ground truth images are acquired by the second modality, wherein the second pairs of complementary images and the second ground truth images represent a second view of the region of interest;
  training a combinational network to combine features from the first and second models; and
  generating at least one synthetic second modality image by passing current images through the trained first or second model and the combinational network, wherein the current images are acquired by the first modality and represent the first or second view of the region of interest.

19. The one or more non-transitory computer-readable media of claim 18 wherein the first and second modalities are different.

20. The one or more non-transitory computer-readable media of claim 18 wherein the first and second modalities are same.

* * * * *